(12) United States Patent
Wang et al.

(10) Patent No.: US 10,529,061 B2
(45) Date of Patent: Jan. 7, 2020

(54) SYSTEMS AND METHODS OF FORMING ENHANCED MEDICAL IMAGES (71) Applicants: Ruikang K. Wang, Seattle, WA (US); Anqi Zhang, Seattle, WA (US)

(72) Inventors: Ruikang K. Wang, Seattle, WA (US); Anqi Zhang, Seattle, WA (US)

(73) Assignee: University of Washington, Seattle, WA (US)

( * ) Notice: Subject to any disclaimer, the term of this patent is extended or adjusted under 35 U.S.C. 154(b) by 199 days.

(21) Appl. No.: 15/751,443

(22) PCT Filed: Aug. 12, 2016

(86) PCT No.: PCT/US2016/046895
§ 371 (c)(1),
(2) Date: Feb. 8, 2018

(87) PCT Pub. No.: WO2017/027844
PCT Pub. Date: Feb. 16, 2017

(65) Prior Publication Data
US 2018/0232864 A1 Aug. 16, 2018

Related U.S. Application Data (60) Provisional application No. 62/204,617, filed on Aug. 13, 2015.

(51) Int. Cl.
*G06T 5/00* (2006.01)
*A61B 3/10* (2006.01)
(Continued)

(52) U.S. Cl.
CPC ............ *G06T 5/004* (2013.01); *A61B 3/0025* (2013.01); *A61B 3/102* (2013.01); *A61B 3/12* (2013.01);
(Continued)

(58) Field of Classification Search
CPC ......... A61B 3/0025; A61B 3/102; A61B 3/12; A61B 3/1233; G06T 2207/10101;
(Continued)

(56) References Cited

U.S. PATENT DOCUMENTS 8,018,598 B2  9/2011  Cense et al.
8,054,468 B2  11/2011  De Boer et al.
(Continued)

FOREIGN PATENT DOCUMENTS

WO  2014040070 A1  3/2014

OTHER PUBLICATIONS

A. Mariampillai, et al., "Speckle variance detection of microvasculature using swept-source optical coherence tomography," Opt. Lett. 33(13), 1530-1532 (2008).
(Continued)

*Primary Examiner* — Yon J Couso
(74) *Attorney, Agent, or Firm* — Perkins Coie LLP (57) ABSTRACT Systems and methods of producing medical images of a subject are disclosed herein. In one embodiment, structural data and vascular data are acquired from a region of interest in the subject. A filter is generated using structural image data acquired from a second layer and blood flow image data received from a first layer in the region of interest. The filter is applied to vascular image data acquired from a second, deeper layer in the region of interest to form an image of the second layer having reduced tailing artifacts relative to the unfiltered vascular image data.

20 Claims, 6 Drawing Sheets (51) Int. Cl.
 A61B 3/00 (2006.01)
 A61B 3/12 (2006.01)
 G06T 7/187 (2017.01)
 G06T 7/11 (2017.01)
 G06T 7/00 (2017.01)
(52) U.S. Cl.
 CPC .......... *A61B 3/1233* (2013.01); *G06T 7/0012* (2013.01); *G06T 7/11* (2017.01); *G06T 7/187* (2017.01); *G06T 2207/10028* (2013.01); *G06T 2207/10101* (2013.01); *G06T 2207/30041* (2013.01)
(58) Field of Classification Search
 CPC . G06T 2207/10028; G06T 2207/30041; G06T 5/004; G06T 7/11; G06T 7/187; G06T 7/0012
 See application file for complete search history.

(56) References Cited

U.S. PATENT DOCUMENTS

| | | | |
|---|---|---|---|
| 8,781,214 | B2 | 7/2014 | Davis et al. |
| 10,307,056 | B2* | 6/2019 | Buckland ............ A61B 3/0025 |
| 2002/0188203 | A1 | 12/2002 | Smith et al. |
| 2007/0195269 | A1 | 8/2007 | Wei et al. |
| 2012/0070049 | A1 | 3/2012 | Iwase et al. |
| 2012/0127427 | A1 | 5/2012 | Guo et al. |
| 2015/0201829 | A1 | 7/2015 | Reisman et al. |
| 2016/0228000 | A1* | 8/2016 | Spaide .................... G06T 15/08 |
| 2017/0119242 | A1* | 5/2017 | Jia ........................ A61B 3/0025 |

OTHER PUBLICATIONS

A. Zhang et al., "Feature space optical coherence tomography based micro-angiography," Biomed. Opt. Express 6(5), 1919-1928 (2015).
B. J. Vakoc, et al., "Cancer imaging by optical coherence tomography: preclinical progress and clinical potential," Nat. Rev. Cancer 12(5), 363-368 (2012).
D. M. Schwartz, et al., "Phase-variance optical coherence tomography: a technique for noninvasive angiography," Ophthalmology. 121(1), 180-187 (2014).
D. Y. Kim, et al., "Optical imaging of the chorioretinal vasculature in the living human eye," Proc. Natl. Acad. Sci. 110(35), 14354-14359 (2013).
E. Jonathan, et al., "Correlation mapping method for generating microcirculation morphology from optical coherence tomography (OCT) intensity images," J. Biophotonics 4(9), 583-587 (2011).
E. Moult, et al., "Ultrahigh-Speed Swept-Source OCT Angiography in Exudative AMD," Ophthalmic Surg Lasers Imaging Retina. 45(6), 496-505 (2014).
I. Fukushima, et al., "Comparison of indocyanine green and fluorescein angiography of choroidal neovascularization," Jpn. J. Ophthalmol. 41(5), 284-296 (1997).
J. Ambati, et al., "Age-Related Macular Degeneration: Etiology, Pathogenesis, and Therapeutic Strategies," Surv. Ophthalmol. 48(3), 257-293 (2003).
J. Fingler, et al., "Mobility and transverse flow visualization using phase variance contrast with spectral domain optical coherence tomography," Opt. Express 15(20), 12636-12653 (2007).
J. Qin, et al. "In vivo volumetric imaging of microcirculation within human skin under psoriatic conditions using optical microangiography." Lasers in Surgery and Medicine 43(2): 122-129 (2011).
L. An, et al., "Ultrahigh sensitive optical microangiography for in vivo imaging of microcirculations within human skin tissue beds," Opt. Express 18(8), 8220-8228 (2010).
Lee, K. K. C., et al., (2012). Real-time speckle variance swept-source optical coherence tomography using a graphics processing unit. Biomedical Optics Express, 3(7), 1557.
M. Friebel, et al., "Determination of optical properties of human blood in the spectral range 250 to 1100nm using monte carlo simulations with hematocrit-dependent effective scattering phase functions," J. Biomed. Opt. 11(3), 034021 (2006).
M. P. López-Sáez, et al., "Fluorescein-Induced Allergic Reaction," Ann. Allergy Asthma Immunol. 81(5), 428-430 (1998).
M. R. Thorell, et al. "Swept-Source OCT Angiography of Macular Telangiectasia Type 2," Opthalmic Surg Lasers Imaging Retina, 45(5), 369-380 (2014).
P. E. Stanga, et al., "Indocyanine green angiography in chorioretinal diseases: indications and interpretation: An evidence-based update," Ophthalmology, 110(1), 15-21 (2003).
R.K. Wang, "Signal degradation by multiple scattering in optical coherence tomography of dense tissue: a Monte Carlo study towards optical clearing of biotissues", Phys. Med. Biol. 47(13), 2281-2299 (2002).
R.K. Wang, et al., "Depth-resolved imaging of capillary networks in retina and choroid using ultrahigh sensitive optical microangiography", Optics Letters 35 (9), 1467-1469 (2010).
S. Dziennis, et al., "Macro-to-micro cortical vascular imaging underlies regional differences in ischemic brain", Scientific Reports, 5, 10051; doi: 10.1038/srep10051 (2015).
T. Y. Wong, et al., "Myopic choroidal neovascularisation: current concepts and update on clinical management", Br. J. Ophthalmol. 99, 289-296 (2015).
U. Baran, et al., "Vasodynamics of pial and penetrating arterioles in relation to arterioloarteriolar anastomosis after focal stroke", Neurophotonics 2(2), 025006 (2015).
V.V. Tuchin, et al., "Dynamic optical coherence tomography in studies of optical clearing, sedimentation, and aggregation of immersed blood", Applied Optics, 41, 258-271 (2002).
W.J. Choi, et al., "Optical coherence tomography microangiography for monitoring the response of vascular perfusion to external pressure on human skin tissue", J Biomed Opt 19(5), 056003 (May 2014).
X. Yin, et al., "User-guided segmentation for volumetric retinal optical coherence tomography images", Journal of Biomedical Optics, 19(8), 086020 (2014).
Y. J. Hong, et al., "Noninvasive investigation of deep vascular pathologies of exudative macular diseases by high-penetration optical coherence angiography," Invest. Ophthalmol. Vis. Sci. 54(5), 3621-3631 (2013).
Y. Jia, et al., "Split-spectrum amplitude-decorrelation angiography with optical coherence tomography," Opt. Express 20(4), 4710-4725 (2012).
Y. Li, et al., "Application of Thinned-Skull Cranial Window to Mouse Cerebral Blood Flow Imaging Using Optical Microangiography," PLoS ONE 9(11), 0113658 (2014).
Zhang et al., "Minimizing projection artifacts for accurate presentation of choroidal neovascularization in OCT micro-angiography", Biomed Opt Express. Oct. 1, 2015; 6(10): 4130-4143.
International Search Report and Written Opinion dated Oct. 21, 2016 in International Patent Application No. PCT/US2016/046895. 11 pages.

\* cited by examiner

SYSTEMS AND METHODS OF FORMING ENHANCED MEDICAL IMAGES

CROSS-REFERENCE TO RELATED APPLICATION(S)

This application is a U.S. National Phase Application under 35 U.S.C. § 371 of International Application No. PCT/US16/46895, filed Aug. 12, 2016, which claims priority to U.S. Provisional Application No. 62/204,617, filed Aug. 13, 2015, the disclosures of which are incorporated herein by reference in their entireties.

STATEMENT REGARDING FEDERALLY SPONSORED RESEARCH

This invention was made with government support under Grant No. R01 EY024158, awarded by the National Eye Institute. The government has certain rights in the invention.

TECHNICAL FIELD

The present application generally relates to medical imaging. In particular, some embodiments include systems and methods of constructing and enhancing optical coherence tomography images of tissue in a subject.

BACKGROUND

The outer portion of a human eye has several layers including the sclera, which is an outer layer, and the retina, which is a light-sensitive inner layer. The choroid is a layer between the sclera and the retina that includes blood vessels and connective tissue. The choroid includes an inner layer referred to as the Bruch's membrane that is adjacent an outer layer of the retina referred to as the retinal pigment epithelium (RPE). In some instances, Choroidal Neovascularization (CNV) occurs in which abnormal new blood cells grow in the choroid that penetrate the Bruch's membrane and extend through the RPE into the retina. CNV can cause vision loss and/or impairment and is involved in a number of retinal diseases such as, for example, age-related macular degeneration (AMD) and high myopia. Early detection and monitoring of CNV can be significantly helpful in controlling disease progression.

Conventional approaches for detecting CNV include, for example, fluorescein angiography (FA) and indocyanine green angiography (ICGA). Both FA and ICGA have drawbacks, however. Neither modality is depth resolved and thus determination of neovascularization caused by CNV is typically based on a clinician's judgment rather than quantitative results. Furthermore, both FA and ICGA require intravenous dye injection, which can result in nausea and other side effects, and may not be available for repeated use on patients. Optical coherence tomography (OCT) micro-angiography (OCTA) is another imaging modality that can be used to detect CNV. OCTA can have advantages over FA and ICGA (and other approaches) in that OCTA can provide localized depth information and can be performed without administering a contrast agent. In many OCTA images, however, a tailing effect from overlaying blood vessels can lead to strong image artifacts appearing in the results of blood vessel networks within the outer retinal space and choroid. These image artifacts can significantly hinder the ability to visualize and interpret 3D angiographic results, thereby reducing the effectiveness of OCTA as a tool for CNV diagnosis.

DETAILED DESCRIPTION

The present technology relates generally to producing medical images of a region of interest of a subject. In one embodiment of the present technology, for example, a method of generating an enhanced medical image of a region of interest (e.g., an eye, brain, skin and/or another organ) of a subject (e.g., a human, an animal) includes acquiring volumetric image data (e.g., OCT data, ultrasound data, medical resonance imaging (MRI) data, radiological data) from the region of interest. The volumetric image data can include structural image data and vascular image data acquired from a plurality of layers (e.g., one or more layers in a retina of an eye) in the region of interest. A mask is generated using vascular image data acquired from a first layer (e.g., an upper layer of the retina) and structural image data acquired from a second layer (e.g., a deeper layer of the retina) the plurality of layers. In certain aspects, for example, a portion of the second layer laterally overlaps the structural image data acquired from the first layer. The mask can be applied to vascular image data acquired from at least a second layer (e.g., a layer in the retina deeper than the upper layer) of the plurality of layers. An enhanced image is formed from the masked vascular image data. In one aspect, for example, the enhanced image is relatively free of tailing artifacts compared to unmasked images. In some aspects, the structural image data acquired from the second layer is normalized (e.g., normalized to a range between 0 and 1). The normalization operation may be operated in linear scale or non-linear scale. The normalized structural image data can be multiplied by vascular image data acquired from the first layer to generate the mask. In certain aspects, the mask is generated using structural image data acquired from the second layer and from one or more additional layers of the plurality of layers.

In another embodiment of the present technology, a method of operating a medical imaging system to construct an OCT image of a region of interest (e.g., a retina of an eye) of a subject (e.g., a human or an animal) includes transmitting a plurality of light pulses from a laser light source toward the region of interest. A detector optically coupled to the laser light source receives backscattered light from the region of interest. The detector generates signals indicative of backscattered light received at the detector from the region of interest, and structural data and blood flow data are acquired from the generated signals. The acquired data is segmented into a first layer (e.g., an upper layer of the retina) and at least a second layer (e.g., a layer in the retina that is deeper than the first layer relative to the region of interest). Blood flow data acquired from the second layer is filtered using structural data acquired from the second layer and blood flow data from the first layer. A filtered image of the second layer is constructed using the filtered blood flow data from the second layer. In some aspects, filtering the blood flow data acquired from the second layer includes normalizing the structural data received from the second layer, and further includes multiplying blood flow data acquired from the first layer by the normalized structural image data acquired from the second layer. In other aspects, however, the filtering can include calculating a difference between the blood flow data received from the second layer and a weighted portion of the blood flow data received from the first layer, and further includes multiplying normalized structural image data acquired from the second layer. In another aspect, the filtering can be performed using normalized structural data acquired from the first layer, the second layer and from the one or more additional. In some aspects, the filtered image of the second layer includes fewer tailing artifacts relative to the unfiltered blood flow data acquired from the second layer.

In yet another embodiment of the present technology, a medical imaging system includes a light source configured to produce laser light and an imaging module optically coupled to the light source. The imaging module is configured to direct the laser light toward a region of interest (e.g., an eye) in the subject (e.g., a human or an animal) and further configured to receive backscattered light from the subject. A detector optically coupled to the imaging module is configured to produce electrical signals that correspond to light received from the imaging A processor and memory are operatively coupled to the detector. The memory includes instructions that, when executed by the processor, are configured to perform various operations including, for example, acquiring structural data and blood flow data from the region of interest using the signals produced by the detector. The memory further includes instructions for segmenting the acquired data into a first layer and at least a second layer deeper than the first The memory also includes instructions for filtering blood flow data acquired from the second layer using structural data acquired from the second layer and blood flow data acquired from the first layer, and for constructing a filtered image of the second layer using the filtered blood flow data from the second layer. In some aspects, filtering the blood flow data further includes multiplying normalized structural data received from the second layer by blood flow data acquired from the first layer. In other aspects, however, filtering the blood flow data includes subtracting a weighted portion of the blood flow data received from the first layer from the blood flow data, and further include multiplying the normalized structural data from the second layer. In certain aspects, filtering the blood flow data further includes applying structural data acquired from the first layer, the second layer and from one or more additional layers.

These and other aspects of the present technology are described in greater detail below. Certain details are set forth in the following description and in FIGS. 1-6D to provide a thorough understanding of various embodiments of the present technology. Other details describing well-known systems and methods often associated with producing medical images (e.g., OCT images), and/or utilizing image processing techniques have not been set forth in the following disclosure to avoid unnecessarily obscuring the description of the various embodiments.

Figure 1A:
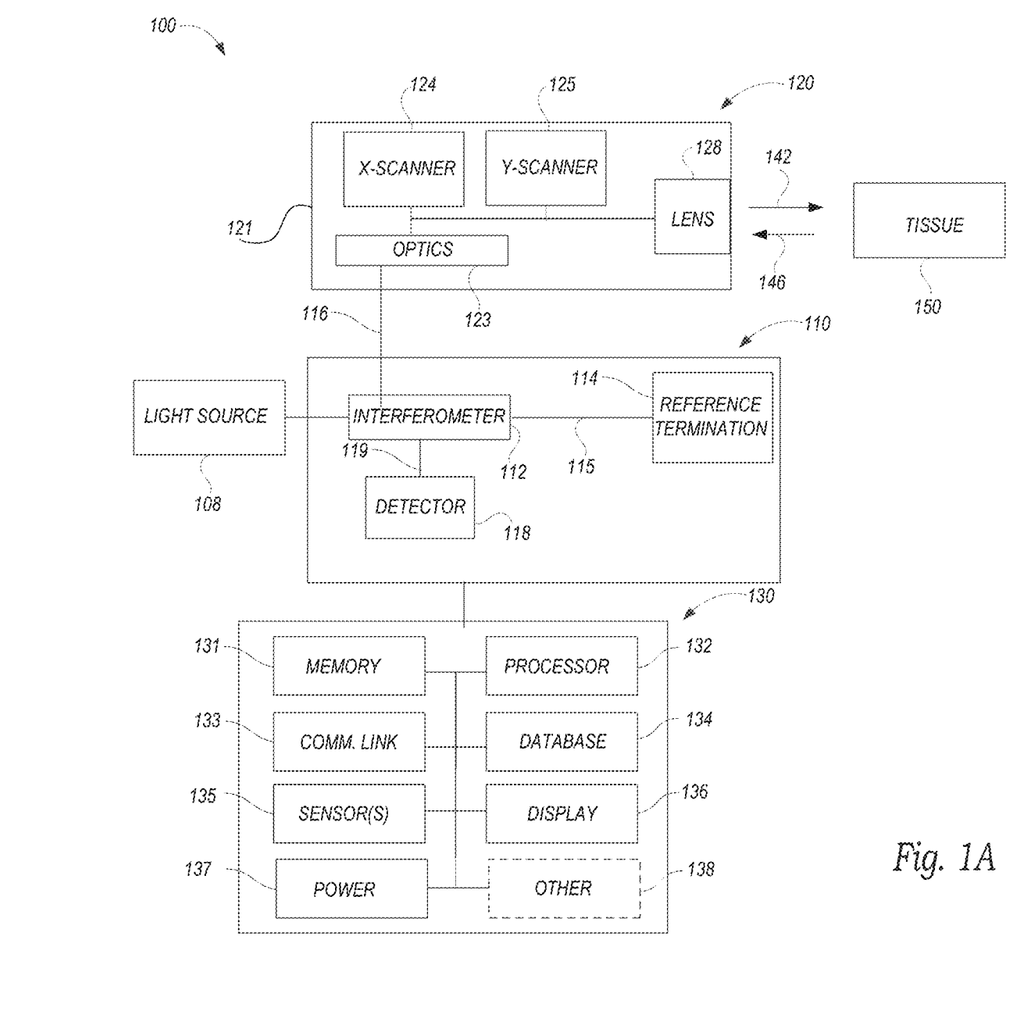
FIG. 1A is a schematic diagram of a medical imaging system configured in accordance with embodiments of the present technology.

In the Figures, identical reference numbers identify identical, or at least generally similar, elements. To facilitate the discussion of any particular element, the most significant digit or digits of any reference number refers to the Figure in which that element is first introduced. For example, element 110 is first introduced and discussed with reference to FIG. 1. Many of the details, dimensions, angles and other features shown in the Figures are merely illustrative of particular embodiments of the disclosed technology. Accordingly, other embodiments can have other details, dimensions, angles and features without departing from the spirit or scope of the disclosure. In addition, those of ordinary skill in the art will appreciate that further embodiments of the invention can be practiced without several of the details described below.

Suitable System(s)

FIG. 1A is a block diagram of an imaging system 100 configured in accordance with an embodiment of the disclosed technology. The system 100 includes an imaging module 110 coupled to a light source 108 and a computer or a processing subsystem 130. A sample arm 116 (e.g., a cable comprising one or more optical fibers) couples an imaging probe 120 to the imaging module 110. As explained in further detail below, the system 100 can be configured to produce optical coherence tomography (OCT) images of tissue using light 142 directed toward tissue 150 and backscattered light 146 received from the tissue 150 (e.g., a human eye) via the probe 120. The backscattered light 146 can be used by the processing subsystem 130 to form OCT images that show a flow of blood through portions (e.g., the retina) of the tissue 150.

The probe 120 includes a housing or an enclosure 121 configured to house image optics 123 that optically couple the probe 120 to the imaging module 110. The optics 123 may include, for example, one or more lenses, collimators, splitters, prisms and/or optical filters. In some embodiments, the optics 123 can include an optical filter configured to attenuate noise and other artifacts caused by reflections along a cavity. An x-scanner 124 and a y-scanner 125 (e.g., x-y galvanometric scanners) in the probe 120 are configured to perform scans of a region of interest in the subject. A lens 128 is configured to focus and/or direct laser light 142 received from the light source 108 via the imaging module 110 toward the region of interest. The lens 128 is further configured to direct backscattered light 146 received from the region of interest toward the x-scanner 124 and/or the y-scanner 125. In some embodiments, the lens 128 includes a 5× telecentric lens. In one embodiment, the lens 128 may include, for example, an LSM03 lens having a working distance of 25.1 mm and manufactured by Thorlabs Inc. In other embodiments, however, the lens 128 can include any lens suitable for OCT imaging.

The light source 108 can include a swept-source laser configured to output laser The light source 108 can be configured, for example, to sweep the laser wavelength across a broad spectral range near 1300 nm at a fixed repetition rate of 100 kHz. In some embodiments, the light source 108 includes a MEMS-tunable vertical cavity surface-emitting laser. In one embodiment, the light source 108 includes, for example, a SL1310V1-10048 model laser manufactured by Thorlabs Inc. In other embodiments, however, the light source 108 may include any light source suitable for OCT imaging. The light source 108 is configured to emit an output beam (e.g., a 28 mW laser output beam) toward an interferometer 112 in the imaging module 110 optically coupled to the probe 120 via the sample arm 116. The interferometer 112 (e.g., a Mach-Zehnder interferometer and/or any suitable Michelson-type interferometer) is coupled to a reference 114 (e.g., a mirror) via a reference arm 115 (e.g., a cable, a conduit and/or one or more optical fibers). A detector 118 (e.g., a gain-balanced photo-detector, a spectrometer) is optically coupled to the interferometer 112 via optics 119 (e.g., one or more lens, collimators, beam splitters, diffraction gratings, transmission gratings). The detector 118 is configured to produce one or more electrical signals that generally correspond to and/or are indicative of intensities of light signals received from the interferometer 112. In some embodiments, the light signals include an interference signal resulting from a combination in the interferometer 112 of light reflected from the reference 114 and backscattered light 146 received from the region of interest via the probe 120. As described in further detail below, the processing subsystem 130 is configured to receive the electrical signals produced by the detector 118 and acquire one or more sets of image data to produce one or more medical images.

Processing Subsystem

The following discussion provides a brief, general description of a suitable environment in which the technology may be implemented. Although not required, aspects of the technology are described in the general context of computer-executable instructions, such as routines executed by a general-purpose computer. Aspects of the technology can be embodied in a special purpose computer or data processor that is specifically programmed, configured, or constructed to perform one or more of the computer-executable instructions explained in detail herein. Aspects of the technology can also be practiced in distributed computing environments where tasks or modules are performed by remote processing devices, which are linked through a communication network (e.g., a wireless communication network, a wired communication network, a cellular communication network, the Internet, a short-range radio network (e.g., via Bluetooth)). In a distributed computing environment, program modules may be located in both local and remote memory storage devices.

Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g. a Bluetooth network) on a propagated signal on a propagation medium (e.g., an electromagnetic wave(s), a sound wave) over a period of time, or may be provided on any analog or digital network (packet switched, circuit switched, or other scheme).

The processing subsystem 130 includes several components including memory 131 (e.g., one or more computer readable storage modules, components, devices) and one or more processors 132. The memory 131 can be configured to store information (e.g., image data, subject information or profiles, environmental data, data collected from one or more sensors, media files) and/or executable instructions that can be executed by the one or more processors 132. The memory 131 can include, for example, instructions for forming, processing, or otherwise constructing medical images of a region of interest using electrical signals produced by the detector 118 that are indicative of intensities of coherent backscattered light received from the region of interest. The medical images may include, for example, one or more two-dimensional images, three-dimensional images and/or video clips comprising a graphical representation of blood perfusion and/or vascular architecture of the region of interest. As described in further detail below, the memory 131 also includes instructions for enhancing medical images including instructions, for example, for decomposing OCT image data into structural and vascular data, segmenting OCT image data into a plurality of layers, normalizing structural data and/or applying masks or filters to vascular image data. Executing instructions for enhancing the medical images may result in enhanced medical images having fewer artifacts (e.g., OCT tailing artifacts) relative to unenhanced images.

The processing subsystem 130 also includes communication components 133 (e.g., a wired communication link and/or a wireless communication link (e.g., Bluetooth, Wi-Fi, infrared and/or another wireless radio transmission network)) and a database 134 configured to store to data (e.g., image data acquired from the region of interest, equations, filters) used in the generation of medical images. One or more sensors 135 can provide additional data for use in image processing and/or construction. The one or more sensors 135 may include, for example, one or more ECG sensors, blood pressure monitors, galvanometers, accelerometers, thermometers, hygrometers, blood pressure sensors, altimeters, gyroscopes, magnetometers, proximity sensors, barometers and/or hall effect sensors. One or more displays 136 can provide video output and/or graphical representations of images formed by the system 100. A power supply 137 (e.g., a power cable connected to a building power system, one or more batteries and/or capacitors) can provide electrical power to components of the processing subsystem 130 and/or the system 100. In embodiments that include one or more batteries, the power supply 137 can be configured to recharge, for example, via a power cable, inductive charging, and/or another suitable recharging method. Furthermore, in some embodiments, the processing subsystem 130 may one or more additional components 138 (e.g., one or more microphones, cameras, Global Positioning System (GPS) sensors, Near Field Communication (NFC) sensors).

In some embodiments, the processing subsystem 130 may comprise one or more components that are partially or wholly incorporated into the imaging module 110 and/or the probe 120. In other embodiments, however, the processing subsystem 130 may include components that are remote from the imaging module 110 and/or the probe 120 and connected thereto by a communication network (e.g., the Internet and/or another network). In some embodiments, for example, at least a portion of the processing subsystem 130 may reside on a mobile device (e.g., a mobile phone, a tablet, a personal digital assistant) and/or a computer (e.g., a desktop computer, a laptop) communicatively coupled to the imaging module 110 and/or the probe 120.

Suitable Environment

Figure 1B:
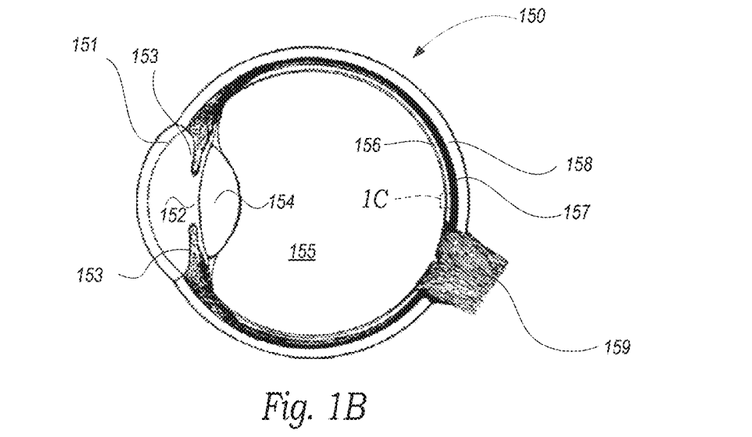
FIG. 1B is a cross sectional schematic diagram of a human eye.
Figure 1C:
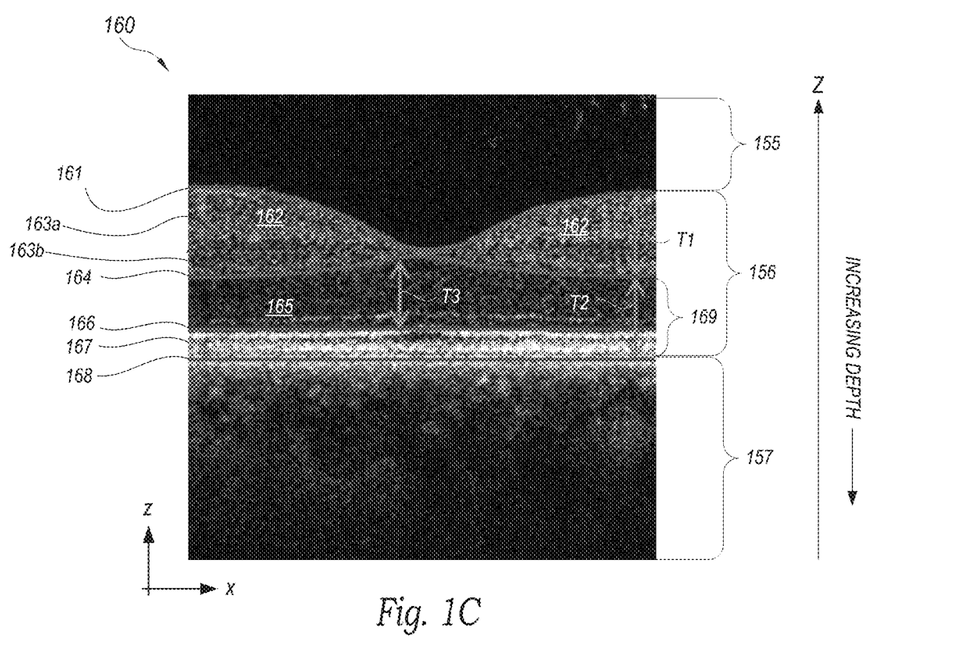
FIG. 1C is an enlarged portion of FIG. 1B showing certain structures of a human eye.

FIG. 1B is a schematic diagram showing a cross sectional side view of the tissue 150 (e.g., a human eye) of the subject. FIG. 1C is an image frame 160 showing an enlarged cross section side view of a portion of FIG. 1B showing certain structures of the tissue 150. Referring first to FIG. 1B, the tissue 150 includes a cornea 151, a pupil 152, an iris 153 and a lens 154. Vitreous humor 155 in a center portion of the tissue 150 separates the lens 154 from the retina 156. A choroid 157 is positioned between the retina 156 and a sclera 158. An optic nerve 159 transmits visual information from the retina 156 toward the subject's brain.

Referring now to FIG. 1C, the image frame 160 includes several structures of the retina 156 and the choroid 157. The retina 156 includes an inner limiting membrane (ILM) 161, an outer plexiform layer (OPL) 164 and other physiological layers. A retinal space 162 between the ILM 161 and the OPL 164 has a thickness T1 (e.g., between about 10 microns and about 300 microns, or approximately 150 microns) and includes a superficial retina layer 163a and a deep retina layer 163b. An inner and outer photoreceptor segment (IS/OS) layer 166 separates a subretina above the IS/OS layer 166 and a retinal pigment epithelium layer 167. The subretina above the IS/OS layer 166 and a retinal pigment epithelium layer 167 can be collectively known as a subretina 169 and have a thickness T2 (e.g., between about 10 microns and about 300 microns, or approximately 150 microns). The subretina above the IS/OS layer 165 can have a thickness T3 (e.g., between about 10 microns and about 140 microns, or approximately 140 microns). A Bruch's membrane 168 separates the retina 156 and the choroid 157.

As described in more detail below, a Choroidal Neovascularization (CNV) can occur when new blood vessels abnormally form (not shown) in the choroid 157, penetrate the Bruch's membrane 168 and extend into the subretina 169. A CNV in the subretina 169 can significantly impair vision in the subject and some instances result in partial or total vision loss. Blood flow in a vascular image of the subretina 169 can be indicative of a CNV because a subretina is generally avascular in the healthy retina. In some OCT images, however, tailing artifacts in a vascular image of the subretina 169 can interfere with interpretation of the images to determine whether a CNV is indeed present. Embodiments of the present disclosure can be used to form enhanced images having minimized or reduced tailing artifacts, thereby resulting in better visualization of the subretina 169 and/or detection of CNVs in the retina.

Suitable Methods

Figure 2A:
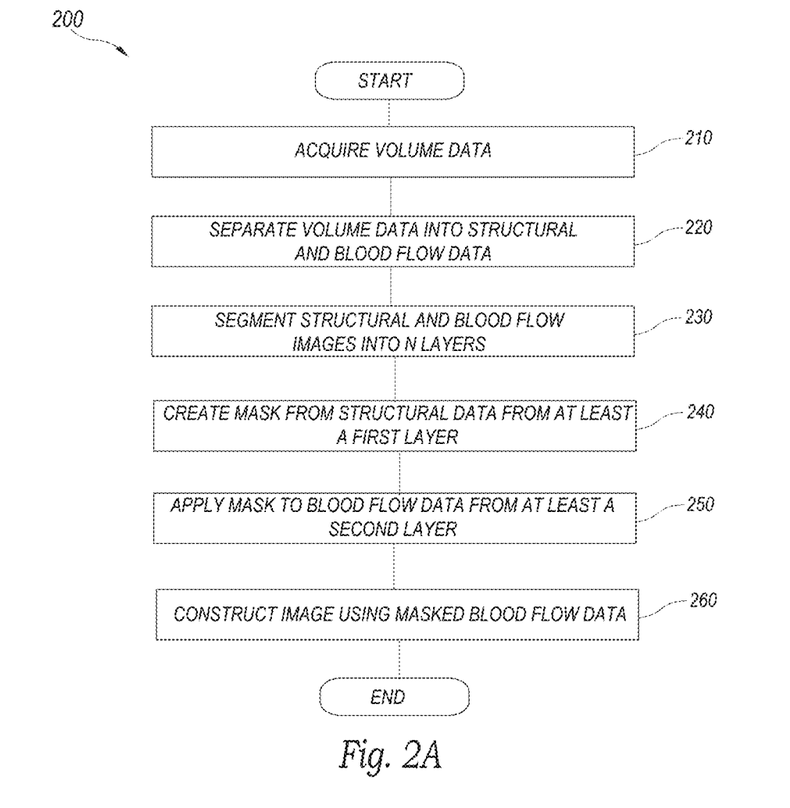
FIG. 2A is a flow diagram of a process configured in accordance with an embodiment of the present technology.

FIG. 2A is a flow diagram of a process 200 configured in accordance with an embodiment of the present technology. The process 200 can comprise instructions stored, for example, on the memory 131 of the system 100 (FIG. 1A) that are executable by the one or more processors 132 (FIG. 1A). In some embodiments, portions of the process 200 are performed by one or more hardware components (e.g., the light source 108 and/or the imaging module 110 of FIG. 1A). In certain embodiments, portions of the process 200 are performed by a device external to the system 100 of FIG. 1A.

At block 210, the process 200 acquires volumetric data from the region of interest (e.g., a retina of a subject's eye). In one embodiment, for example, the process 200 transmits laser light from a light source (e.g., the light source 108 of FIG. 1A) via an imaging module (e.g., the imaging module 110 of FIG. 1A) toward a region of interest (e.g., a retina of a subject's eye). The process 200 receives backscattered light from the region of interest at a detector (e.g., the detector 118 of FIG. 1A), which generates electrical signals indicative of the backscattered light received by the detector. The process 200 can use the generated signals to construct a volumetric data set.

In some embodiments, for example, the process 200 is configured to acquire a plurality (e.g., 400) of A-line scans in one direction (e.g., an x-direction) relative to the region of interest and B-frame scans in another direction (e.g., a y-direction) relative to the region of interest. The process 200 performs a fast B-scan in a y-direction relative to the region of interest to obtain a B-frame containing a plurality (e.g., 400) of A-lines at a predetermined imaging rate (e.g., 100 frames per second (FPS), 180 FPS, 400 FPS). The process 200 further performs a slow C-scan in the Y-direction to obtain a plurality (e.g., 400) of B-frames with a predetermined number (e.g., 24) of repetitions at the each location. Once the scans are completed, the process 200 can produce the volume data including an OCT data cube having a plurality of voxels corresponding to the region of interest.

At block 220, the process 200 separates the acquired volume data into a structural data set and a blood flow (i.e., vascular) data set. In some embodiments, the process 200 can use an eigenvalue decomposition method to form the structural and blood flow data sets from the acquired volume data. In other embodiments, however, the process 200 uses another suitable method to perform the separation into structural and blood flow data sets.

At block 230, the process 200 segments the structural and blood flow data into a predetermined number n (e.g., 5, 10, 20, 30) layers each having a thickness (e.g., between about 10 microns and about 100 microns, between about 15 microns and about 50 microns, or about 30 microns) in the z-direction (i.e., the depth direction relative the region of interest). In some embodiments, the process 200 executes a sorted maximum intensity projection (sMIP) algorithm to segment the structural and blood flow data. In other embodiments, however, the process 200 uses another suitable algorithm to perform the structural and blood flow segmentation.

At block 240, the process 200 generates a mask or filter using blood flow data acquired from at least a first layer (e.g., the retinal space 162 of FIG. 1C) and structural data acquired from at least a second, deeper layer (e.g., the subretina 169 of FIG. 1C) that can be applied to blood flow data received from a second, deeper layer (e.g., the subretina 169 of FIG. 1C). A mask or filter generated from structural data from the second layer and blood flow data from the first layer can be used to reduce tailing artifacts in blood flow data received from the second layer.

At block 250, the process 200 applies the mask to the blood flow data received from the second layer. In one embodiment, the process applies the mask to the blood flow data as shown in equation 1 below:

$$\log [At] = \log [As] \cdot \{1 - \text{Norm} < \log [Ar] \cdot \{1 - \text{Norm} < \log [Is] >\} >\} \quad (1)$$

In equation 1, At represents the filtered, enhanced signal with reduced or minimized artifacts and As represents blood flow data received from the second layer. Ar represents blood flow data received from the first layer and Is represents structural data received from the second layer. The mask from block 240 is represented by the $\{1-\text{Norm}<\log [Ar]\cdot\{1-\text{Norm}<\log [Is]>\}>\}$ term in equation 1 in which the blood flow data and structural data from the first layer and the second layer are normalized using a normalization operation such that the values are normalized to a range between 0 and 1. The normalization operation may include linear scale normalization, or no-linear scale normalization.

At block 260, the process 200 constructs an image frame of the second layer using the filter, providing the enhanced signal At from block 250 with reduced or minimized artifacts.

Figure 2B:
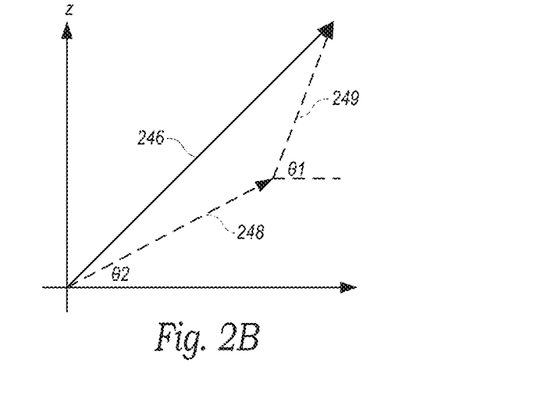
FIG. 2B is a schematic diagram of signals received from a region of interest.

FIG. 2B is a schematic diagram of a signal 246 acquired from a region of interest (e.g., a retina of user's eye) at a predetermined depth in the z-direction in the tissue. The measured signal 246 is shown in FIG. 2B as a vector combination of a backscattered light component 248 having an angle θ2 and a structural component 249 having an angle θ1. The backscattered light component 248 includes effects of light backscattered by red blood cells on the signal 246. The structural component 249 includes the contribution of static tissue (e.g., one or more of the structures of the retina 156 described with respect to FIGS. 1B and 1C) on the signal 246. As discussed above with reference to FIG. 2A, filtering the backscattered light component 248 by subtracting a portion of the structural component 249 can reduce artifacts (e.g., tailing artifacts) caused by interactions of backscattered light with static tissue.

Examples

Figure 3A:
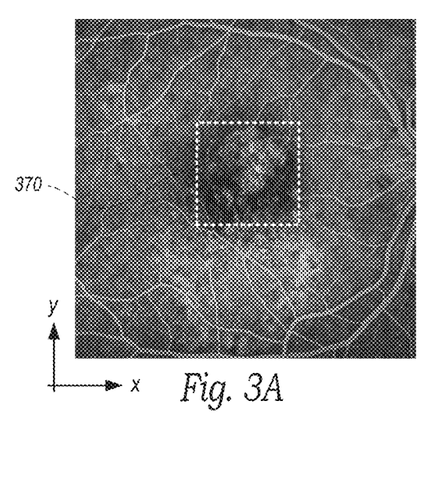
FIG. 3A is a medical fluorescein angiography image of a human eye.
Figure 3B:
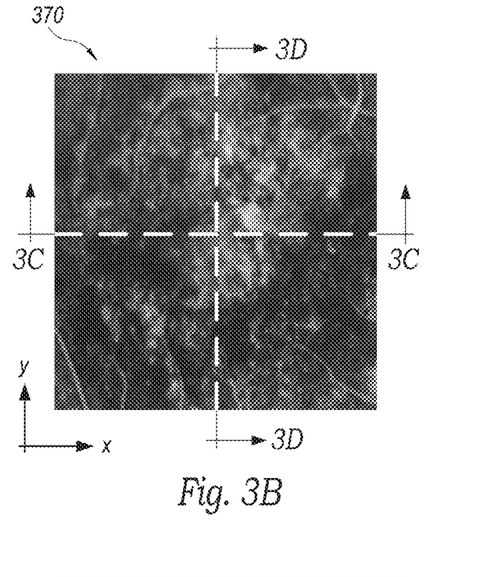
FIG. 3B is an enlarged portion of a region of interest shown in FIG. 3A.
Figure 3C:
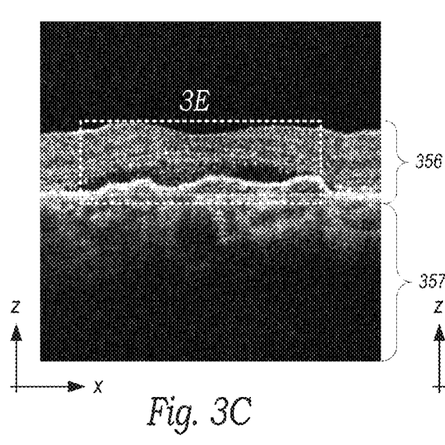
FIG. 3C is a cross sectional OCT image frame along the 3C-3C line in FIG. 3B.
Figure 3D:
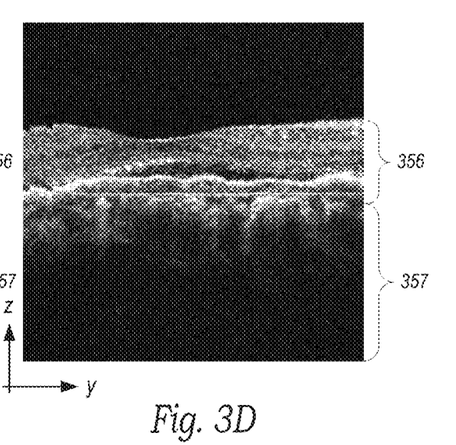
FIG. 3D is a cross sectional OCT image frame along the 3D-3D line in FIG. 3B.
Figure 3E:
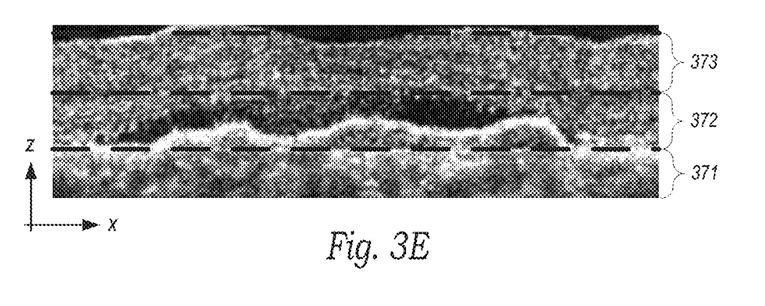
FIG. 3E is an enlarged portion of FIG. 3C.
Figure 4A:
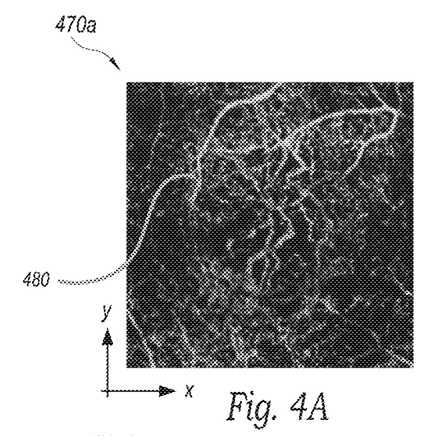
FIGS. 4A-4C are image frames of the region of interest shown in FIG. 3A acquired from corresponding layers in the subject.
Figure 4B:
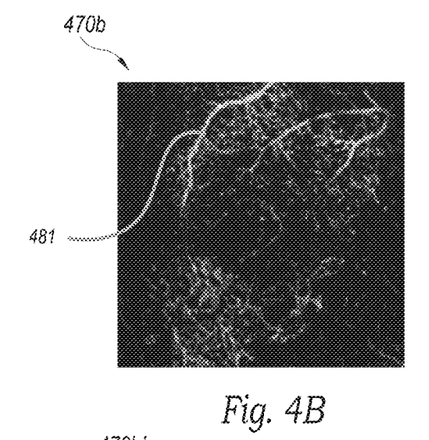
Figure 4C:
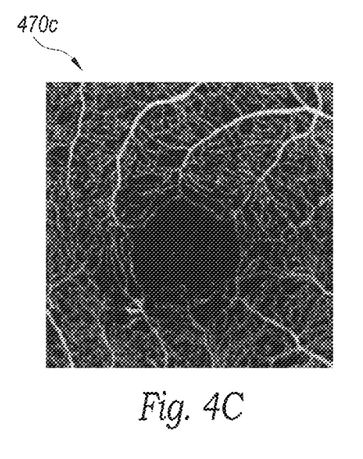
Figure 4D:
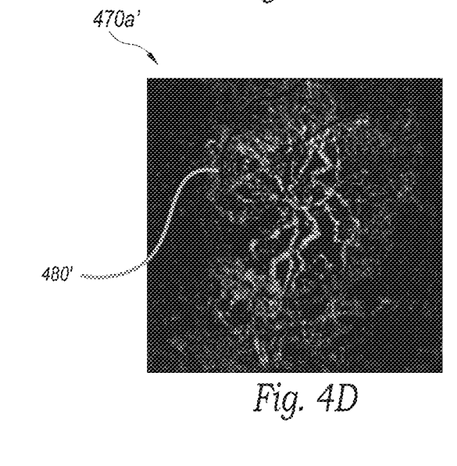
FIGS. 4D and 4E show the image frames of FIGS. 4A and 4B, respectively, after enhancement in accordance with an embodiment of the present technology.
Figure 4E:
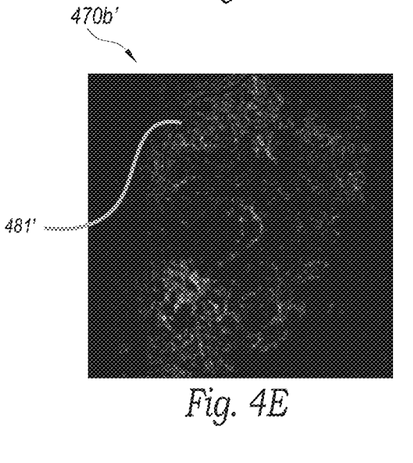
Figure 5A:
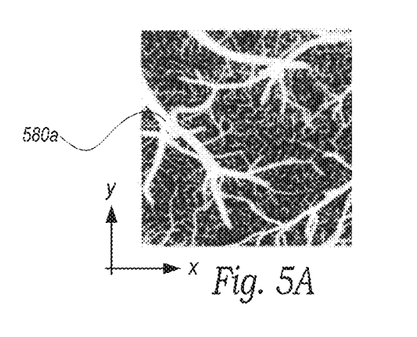
FIGS. 5A-5D are image frames of a region of interest in a subject.
Figure 5B:
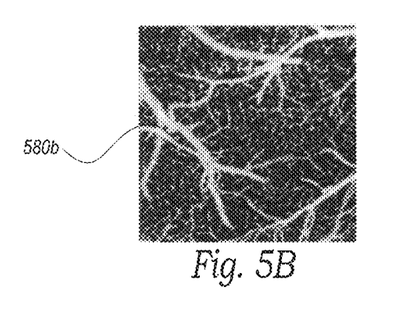
Figure 5C:
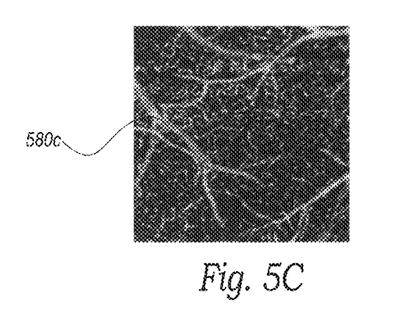
Figure 5D:
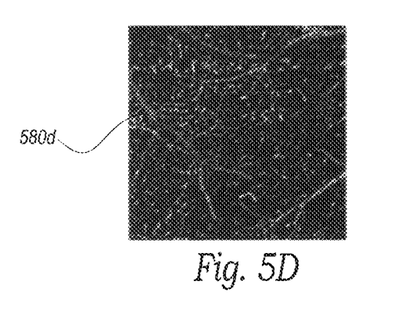
Figure 6A:
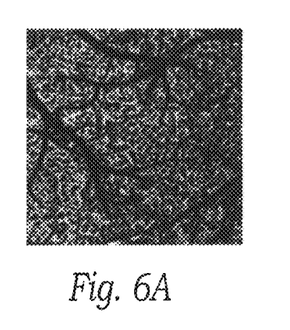
FIGS. 6A-6D shows the image frames of FIGS. 5A-5D, respectively, after enhancement in accordance with an embodiment of the present technology.
Figure 6B:
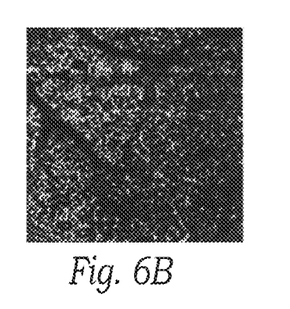
Figure 6C:
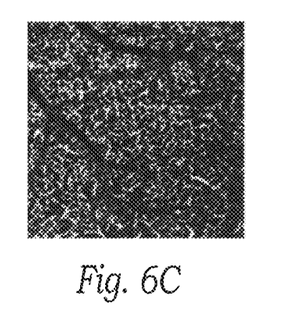
Figure 6D:
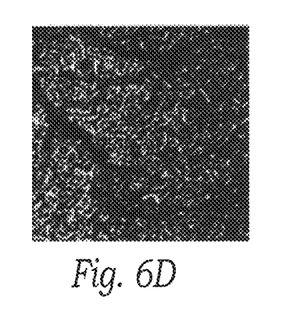

FIG. 3A is a medical fluorescein angiography image of a human eye. FIG. 3B is an enlarged portion of a region of interest 370 shown FIG. 3A. FIG. 3C is a cross sectional OCT image frame along the 3C-3C line in FIG. 3B showing portions of a retina 356 and choroid 357 of the eye. FIG. 3D is a cross sectional OCT image frame along the 3D-3D line in FIG. 3B. FIG. 3E is an enlarged portion of FIG. 3C. FIG. 3E is segmented into a first layer 373, a second layer 372 and a third layer 371. As described above with reference to FIGS. 2A and 2B and further shown in FIGS. 4A-4E, blood flow data obtained from the first layer 373 and structural data from the second layer 372 can be used to construct enhanced image frames of the second layer 372 and the third layer 371 with minimized tailing artifacts. FIGS. 4A-4C show corresponding image frames 470a-c of the layers 371-373 of FIG. 3E. Tailing artifacts 480 are present in the image frame 470a (FIG. 4A) of the third layer 371 (FIG. 3E), and tailing artifacts 481 are present in the image frame 470b (FIG. 4B) of the second layer 372 (FIG. 3E). FIG. 4C shows a blood flow image frame 470c of the first layer 373. FIG. 4D shows an image frame 470a' of the third layer 371 (FIG. 3E) with reduced tailing artifacts 480' after enhancement in accordance with embodiments of the present technology. FIG. 4E shows an image frame 470b' of the second layer 372 (FIG. with reduced tailing artifacts 480' after enhancement in accordance with embodiments of the present technology.

FIGS. 5A-5D are image frames of a different region of interest in a different subject acquired from different depths in the region of interest having corresponding artifacts 580a-580d. FIGS. 6A-6D shows the image frame of FIGS. 5A-5D, respectively, with reduced tailing artifacts after enhancement in accordance with an embodiment of the present technology.

The disclosure may be defined by one or more of the following examples:

1. A method of generating an enhanced medical image of a region of interest of a subject, the method comprising:
acquiring volumetric image data from the region of interest, wherein the volumetric image data includes structural image data and vascular image data acquired from a plurality of layers in the region of interest;
generating a mask using blood flow image data acquired from a first layer of the plurality of layers and structural image data acquired from a second layer of the plurality of layers;
applying the mask to vascular image data acquired from at least a second layer of plurality of layers; and
forming an enhanced image from the masked vascular image data.

2. The method of example 1 wherein generating the mask comprises:
normalizing the structural image data acquired from the second layer; and
multiplying vascular image data acquired from the first layer by the normalized structural image data acquired from the second layer.

3. The method of example 1 or 2 wherein at least a portion of the second layer laterally overlaps the structural image data acquired from the first layer.

4. The method of example 1, 2 or 3 wherein acquiring the volumetric image data comprises:
transmitting light from a light source toward the region of interest;
receiving signals at a detector that are indicative of light backscattered from the region of interest; and
decomposing the received signals into structural image data and vascular image data.

5. The method of any one of examples 1-4 wherein acquiring the volumetric image data comprises segmenting the acquired volumetric image data into a plurality of layers substantially perpendicular to an axial direction relative to the region of interest.

6. The method of any one of examples 1-5 wherein acquiring the volumetric image data comprises acquiring optical coherence tomography microangiography data from the region of interest.

7. The method of any one of examples 1-6 wherein acquiring the volumetric image data comprises acquiring volumetric data from at least a portion of an eye of the subject, wherein the first layer includes a first portion of a retina in the eye and the second layer includes a second portion of the retina, and wherein the second portion of the retina is deeper in an axial direction than the first portion of the retina.

8. The method of any one of examples 1-7 wherein the generating the mask further comprises using structural image data acquired from the second layer and from one or more additional layers of the plurality of layers.

9. A method of operating a medical imaging system to construct an optical coherence tomography (OCT) image of a region of interest of a subject, the method comprising:
transmitting a plurality of light pulses from a laser light source toward the region of interest;
receiving backscattered light from the region of interest at a detector optically coupled to the laser light source;
acquiring data from the region of interest using signals generated by the detector that are indicative of backscattered light received at the detector, wherein acquiring the data includes acquiring structural data and blood flow data from the region of interest;
segmenting the acquired data into a first layer and at least a second layer, wherein the second layer is deeper than the first layer with respect to the region of interest;
filtering blood flow data acquired from the second layer using blood flow data acquired from the first layer and structural data acquired from the second layer; and
constructing a filtered image of the second layer using the filtered blood flow data from the second layer.

10. The method of example 9 wherein the filtering comprises:
normalizing the structural data received from the second layer; and
multiplying blood flow data acquired from the second layer by the normalized structural image data acquired from the second and the normalized blood flow image data from the first layer.

11. The method of example 9 or 10 wherein the filtering comprises calculating a difference between the blood flow data received from the second layer and a weighted portion of the blood flow data received from the first layer, and further comprises multiplying the normalized structural data received from the second layer.

12. The method of example 9, 10 or 11 wherein at least a portion of the second layer is substantially registered with the structural image data acquired from the first layer.

13. The method of any one of examples 9-12 wherein segmenting the acquired image data further comprises segmenting the acquired image data into the first and second layers and one or more additional layers, and further comprising:
combining structural data acquired from the first layer, the second layer and from the one or more additional layers; and
combining blood flow data acquired from the first layer, the second layer and from the one or more additional layers; and
normalizing the combined structural and blood flow data, wherein filtering the blood flow data acquired from the second layer comprises multiplying the blood flow data acquired from the second layer by the normalized structural and blood flow data.

14. The method of any one of examples 9-13 wherein acquiring the data comprises acquiring data from at least a portion of an eye of the subject, and wherein the first layer includes a first portion of a retina in the eye and the second layer includes a second portion of the retina.

15. The method of example 9 wherein acquiring the data comprises acquiring data from at least a portion of a brain of the subject.

16. The method of any one of examples 9-14 wherein the filtered image of the second layer comprises includes fewer tailing artifacts relative to the unfiltered blood flow data acquired from the second layer.

17. A medical imaging system configured to produce images of a subject, the system comprising:
a light source configured to produce laser light;
an imaging module optically coupled to the light source, wherein the imaging module is configured to direct the laser light toward a region of interest in the subject and further configured to receive backscattered light from the subject;
a detector optically coupled to the imaging module, wherein the detector is configured to produce electrical signals that correspond to light received from the imaging module; and
a processor and memory operatively coupled to the detector, wherein the memory includes instructions that, when executed by the processor, are configured to perform the operations of:
acquiring structural data and blood flow data from the region of interest using the signals produced by the detector;
segmenting the acquired data into a first layer and at least a second layer, wherein the second layer is deeper than the first layer with respect to the region of interest;
filtering blood flow data acquired from the second layer using blood flow data acquired from the first layer and structural data acquired from the second layer; and
constructing a filtered image of the second layer using the filtered blood flow data from the second layer.

18. The system of example 17 wherein the memory further includes instructions that, when executed by the processor, are configured to perform the operations of:
normalizing the structural data received from the second layer; and
multiplying blood flow data acquired from the second layer by the normalized structural image data acquired from the second layer and blood flow data acquired from the first layer.

19. The system of example 17 or 18 wherein the memory further includes instructions that, when executed by the processor, are configured to perform the operation of filtering the blood flow data by calculating a difference between the blood flow data received from the second layer and a weighted portion of the blood flow data received from the first layer, and further multiplying the normalized structural data received from the second layer.

20. The system of example 17, 18 or 19 wherein the memory further includes instructions that, when executed by the processor, are configured to perform the operations of:
segmenting the acquired image data into the first and second layers and one or more additional layers;
combining structural data acquired from the first layer, the second layer and from the one or more additional layers;
combining blood flow data acquired from the first layer, the second layer and from the one or more additional layers;
normalizing the combined structural data and combined blood flow data; and
filtering the blood flow data acquired from the second layer by multiplying the blood flow data from the second layer by the normalized structural and blood flow data.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, in some embodiments, the technology can be used, for example, to form images of tissue in a subject's eye and/or brain. In other embodiments, however, the technology may be used to form images of tissue from any portion of a subject's anatomy. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of generating an enhanced medical image of a region of interest of a subject, the method comprising:
    acquiring volumetric image data from the region of interest, wherein the volumetric image data includes structural image data and vascular image data acquired from a plurality of layers in the region of interest;
    generating a mask using vascular image data acquired from a first layer of the plurality of layers and structural image data acquired from a second layer of the plurality of layers;
    applying the mask to vascular image data acquired from at least a second layer of plurality of layers; and
    forming an enhanced image from the masked vascular image data.

2. The method of claim 1 wherein generating the mask comprises:
    normalizing the structural image data acquired from the second layer; and
    multiplying vascular image data acquired from the first layer by the normalized structural image data acquired from the second layer.

3. The method of claim 1 wherein at least a portion of the second layer laterally overlaps the structural image data acquired from the first layer.

4. The method of claim 1 wherein acquiring the volumetric image data comprises:
    transmitting light from a light source toward the region of interest;
    receiving signals at a detector that are indicative of light backscattered from the region of interest; and
    decomposing the received signals into structural image data and vascular image data.

5. The method of claim 1 wherein acquiring the volumetric image data comprises segmenting the acquired volumetric image data into a plurality of layers substantially perpendicular to an axial direction relative to the region of interest.

6. The method of claim 1 wherein acquiring the volumetric image data comprises acquiring optical coherence tomography microangiography data from the region of interest.

7. The method of claim 1 wherein acquiring the volumetric image data comprises acquiring volumetric data from at least a portion of an eye of the subject, wherein the first layer includes a first portion of a retina in the eye and the second layer includes a second portion of the retina, and wherein the second portion of the retina is deeper in an axial direction than the first portion of the retina.

8. The method of claim 1 wherein the generating the mask further comprises using structural image data and blood flow data acquired from the second layer and from one or more additional layers of the plurality of layers.

9. A method of operating a medical imaging system to construct an optical coherence tomography (OCT) image of a region of interest of a subject, the method comprising:
    transmitting a plurality of light pulses from a laser light source toward the region of interest;
    receiving backscattered light from the region of interest at a detector optically coupled to the laser light source;
    acquiring data from the region of interest using signals generated by the detector that are indicative of backscattered light received at the detector, wherein acquiring the data includes acquiring structural data and blood flow data from the region of interest;
    segmenting the acquired data into a first layer and at least a second layer, wherein the second layer is deeper than the first layer with respect to the region of interest;
    filtering blood flow data acquired from the second layer using blood flow data acquired from the first layer and structural data acquired from the second layer; and
    constructing a filtered image of the second layer using the filtered blood flow data from the second layer.

10. The method of claim 9 wherein the filtering comprises:
    normalizing the structural data received from the second layer; and
    multiplying blood flow data acquired from the first layer by the normalized structural image data acquired from the second layer.

11. The method of claim 9 wherein the filtering comprises calculating a difference between the blood flow data received from the second layer and a weighted portion of the blood flow data received from the first layer, and further multiplying the normalized structural data received from the second layer.

12. The method of claim 9 wherein at least a portion of the second layer is substantially aligned with the structural image data acquired from the first layer.

13. The method of claim 9 wherein segmenting the acquired image data further comprises segmenting the acquired image data into the first and second layers and one or more additional layers, and further comprising:
    combining structural data acquired from the first layer, the second layer and from the one or more additional layers; and
    combining blood flow data acquired from the first layer, the second layer and from the one or more additional layers; and
    normalizing the combined structural and blood flow data, wherein filtering the blood flow data acquired from the second layer comprises multiplying the blood flow data acquired from the second layer by the normalized structural and blood flow data.

14. The method of claim 9 wherein acquiring the data comprises acquiring data from at least a portion of an eye of the subject, and wherein the first layer includes a first portion of a retina in the eye and the second layer includes a second portion of the retina.

15. The method of claim 9 wherein acquiring the data comprises acquiring data from at least a portion of a brain of the subject.

16. The method of claim 9 wherein the filtered image of the second layer includes fewer tailing artifacts relative to the unfiltered blood flow data acquired from the second layer.

17. A medical imaging system configured to produce images of a subject, the system comprising:

a light source configured to produce laser light;

an imaging module optically coupled to the light source, wherein the imaging module is configured to direct the laser light toward a region of interest in the subject and further configured to receive backscattered light from the subject;

a detector optically coupled to the imaging module, wherein the detector is configured to produce electrical signals that correspond to light received from the imaging module; and a processor and memory operatively coupled to the detector, wherein the memory includes instructions that, when executed by the processor, are configured to perform the operations of:

acquiring structural data and blood flow data from the region of interest using the signals produced by the detector;

segmenting the acquired data into a first layer and at least a second layer, wherein the second layer is deeper than the first layer with respect to the region of interest;

filtering blood flow data acquired from the second layer using blood flow data acquired from the first layer and structural data acquired from the second layer; and  constructing a filtered image of the second layer using the filtered blood flow data from the second layer.

18. The system of claim 17 wherein the memory further includes instructions that, when executed by the processor, are configured to perform the operations of:

normalizing the structural data received from the second layer; and multiplying blood flow data acquired from the first layer by the normalized structural image data acquired from the second layer.

19. The system of claim 17 wherein the memory further includes instructions that, when executed by the processor, are configured to perform the operation of filtering the blood flow data by calculating a difference between the blood flow data received from the second layer and a weighted portion of the blood flow data received from the first layer, and further multiply the normalized structural data received from the second layer.

20. The system of claim 17 wherein the memory further includes instructions that, when executed by the processor, are configured to perform the operations of:

segmenting the acquired image data into the first and second layers and one or more additional layers;

combining structural data acquired from the first layer, the second layer and from the one or more additional layers;

combining blood flow data acquired from the first layer, the second layer and from the one or more additional layers;

normalizing the combined structural data and the combined blood flow data; and  filtering the blood flow data acquired from the second layer by multiplying the blood flow data from the second layer by the normalized structural and blood flow data.

\* \* \* \* \*